United States Patent [19]
Harju

[11] Patent Number: 6,042,785
[45] Date of Patent: *Mar. 28, 2000

[54] MULTILABEL MEASUREMENT INSTRUMENT

[75] Inventor: Raimo Harju, Turku, Finland

[73] Assignee: Wallac Oy, Turku, Finland

[*] Notice: This patent issued on a continued prosecution application filed under 37 CFR 1.53(d), and is subject to the twenty year patent term provisions of 35 U.S.C. 154(a)(2).

[21] Appl. No.: 08/844,905

[22] Filed: Apr. 22, 1997

[30] Foreign Application Priority Data

Apr. 22, 1996 [FI] Finland ..................................... 961742

[51] Int. Cl.⁷ ................................................... G01N 21/00

[52] U.S. Cl. ....................... 422/52; 422/82.08; 422/82.09

[58] Field of Search ............................ 356/73; 422/82.05, 422/82.08, 82.09, 52

[56] References Cited

U.S. PATENT DOCUMENTS

| | | | |
|---|---|---|---|
| 4,076,420 | 2/1978 | DeMaeyer et al. | 356/73 |
| 4,305,660 | 12/1981 | Kallet | 356/73 |
| 4,531,834 | 7/1985 | Nogami | 356/73 |
| 4,730,922 | 3/1988 | Bach et al. | 356/73 |
| 5,381,224 | 1/1995 | Dixon et al. | 356/72 |
| 5,436,715 | 7/1995 | Fernandes et al. | 356/73 |

*Primary Examiner*—Jeffrey Snay
*Attorney, Agent, or Firm*—Kubovcik & Kubovcik

[57] ABSTRACT

A compact optical instrument for performing various laboratory measurements utilizing different technologies of spectroscopy, i.e., photoluminescence, absorption and chemical luminescence, from liquid and solid samples. The measuring head of the instrument includes a continuous wave lamp unit (cw-lamp unit), a photometric detector unit and an emission unit and further includes an optomechanical coupling unit having at least one movable or replaceable mirror for allowing the optical path of the measurement or optimizing the optical path of the measurement. A controller including electronics and computer interface are also provided.

4 Claims, 12 Drawing Sheets

MULTILABEL MEASUREMENT INSTRUMENT

BACKGROUND OF THE INVENTION

1. Field of the Invention

The present invention relates generally to the field of biochemical laboratory instrumentation for different applications of microtitration plates and corresponding sample supports. More particularly the invention relates to an improved and more complete combination of the instrumental features of fluorometers, photometers and luminometers.

In this patent application the term "photoluminescence" is used to mean "any optical photon emission generated by incident optical radiation". The term "fluorescence" has had the same meaning in older writings but now "fluorescence" should refer purely to molecular processes.

2. Description of Prior Art

The typical instruments in analytical chemical research laboratories are the different spectroscopic instruments. Many of them utilize optical region of the electromagnetic spectrum. The two common type of the instruments are the spectrophotometers and the spectrofluorometers. These instruments comprise usually one or two wavelength dispersion devices, such as monochromators. The dispersion devices make them capable of performing photometric and fluorometric measurements throughout the optical spectrum.

The routine work and also the research work in analytical biochemical laboratories and in clinical laboratories are often based on different tags or labels coupled on macromolecules under inspection. The typical labels used are different radioactive isotopes, enzymes, different fluorescent molecules and e.g. fluorescent chelates of rare earth metals.

The detection of enzyme labels can be performed by utilizing their natural biochemical function, i.e. to alter the physical properties of molecules. In enzyme immunoassays colorless substances are catalyzed by enzymes to colorful substances or non-fluorescent substances to fluorescent substances. That is why the different instrumental methods of measurements are needed.

Biochemical and clinical laboratories have gamma- and betacounters for radioisotopes, filter photometers for colorimetric immunoassays and for clinical chemistry determinations, filter fluorometers for fluorescent immunoassays, luminometers for chemical luminescence, time-resolved fluorometers, etc.

But there are not many instruments on the market which are capable of using more than one measurement technology in the same instrument. Technically all fluorometers are capable of measuring glow-type chemical luminescence but this is not utilized in many instruments.

One of the instruments is a spectrofluorometer by Perkin Elmer Corporation, which spectrofluorometer due to its flash-type excitation lamp and analogue detection method is capable of measuring fluorescence, phosphorescence and luminescence from cuvettes. The said company is supplying a fibre optics option for microtitration plates. However, a spectrofluorometer is intrinsically a far less sensitive instrument than a filter fluorometer and a fibre optics system decreases even more the sensitivity of the instrument.

On the market there is also an instrument named "Fluostar" originally made by BMG LabTechnologies GmbH, Offenburg, Germany. This instrument is capable of measuring conventional fluorescence and time-resolved photoluminescence. It has light guides both in the excitation side and in the emission side and its detection technology is based on the gated analogue often called "boxcar" detection. The use of light guides technology in the emission side and the analogue detection are both the limiting sensitivity of the instrument.

On the market there is also a device including combined photometer and luminometer named "Anthos Lucy" by Labtech International, Uckfield, Great Britain. Also there is coming to the market a combined fluorometer and photometer from Molecular Dynamics, Inc., California. The further perfomance of the devices are not known.

As far as the inventor knows there are no instrumentation for microtitration plates or alike sample supports capable of measuring the following four technologies. The technologies are photoluminescence, absorption, chemical luminescence and time-resolved photoluminescence.

The applicant Wallac company has manufactured time-resolved fluorometers since 1983. The first model of the instrument, called Arcus 1230, was able to count only tubes in racks or strips of microtitration plates in racks. The fluorescent solution was excited through the wall of a tube or a well of the strips. Emission was collected from bottom. The second model Wallac time-resolved fluorometer 1232 was introduced in 1988 and it was able to measure the whole microtitration plate. The excitation optics is situated on the upper side of the plate and it comprises three quartz lenses and filters. The emission optics is below of the sample and it comprises ultra-violet filter and three plastics lenses. Few years later there was introduced a model called 1234 with two additional interference filters in the emission side. However, all these instruments are using only time-resolved photoluminescence measurement technology.

OBJECTS AND SUMMARY OF THE INVENTION

The object of the present invention is to provide a compact optical instrument to perform various laboratory measurements utilizing different technologies of spectroscopy, i.e. photoluminescence, absorption and chemical luminescence from liquid and solid samples arranged in microtitration plates, in other arrangements for plurality wells or in other types of sample supports like filters, gels, etc. used commonly in laboratories.

A further object of the invention is to describe a novel optomechanical arrangement for connecting another lamp to said optical instrument. The lamp is preferably a pulse-lamp, which enlarges the usage of the device into the most sensitive biochemical assays, i.e. time-resolved fluorescence assays.

These objects may be accomplished by providing an apparatus for measuring photon emissions or absorption from different sample supports like microtitration plates, the apparatus comprising:

a continuous wave lamp unit (cw-lamp unit) for photoluminescence excitation and absorption measurement cw-lamp unit including cw-lamp, wavelength selection means and optics i.e light collecting means and light directing means a liquid light guide between the lamp and sample compartment a photometric detector unit for absorption measurements including a light collecting means and detecting means an emission unit including detecting means, wavelength selection means, photon emission collecting and directing means, aperture means for limiting the emission beam an optomechanical coupling unit including reflecting means for directing excitation and photometric light beams the optomechanical coupling unit including a first reflecting means for passing luminescence emission into the detector the optomechanical coupling unit including a second reflecting means for probing a portion of radiation generated by the cw-lamp the optomechanical coupling unit including a stabilizing means for radiation of cw-lamp a plate holder for microtitration plate or other corresponding sample support and plate holder moving means controlling means including electronics and interfacing means for computer Another embodiment of the present invention comprises also:

an optional pulse-lamp unit for time-resolved photoluminescence excitation.

said pulse lamp unit including an excitation pulse generating means, wavelength selection means, a light collecting means and light directing means the said optomechanical coupling unit including an optional dichroic reflecting and transmitting means the said optomechanical coupling unit including an optional second reflecting means the said optomechanical coupling unit including an optional filtering means According to the third embodiment of the present invention the apparatus includes also:

means for adjusting measuring head height

The present invention describes a new versatile non-isotopic optical instrument for different optical measurements in biochemical or clinical laboratories. It enables various types of luminescence and absorption measurements to be preformed on different types of sample well matrixes or on other substrates of the size of the standard microtitration plates.

The optical system of the optical instrument comprises a cw-lamp and an optional pulse-lamp and two detectors and a novel optomechanical coupling unit. By moving the mirror block inside the coupling unit optical paths can be optimized and hence change measuring properties of the instrument.

One usage of this invention is a photoluminescence counter, where a sample is excited from an upper side with either of the lamps. In this respect this invention refers to the instruments usually called platefluorometers.

Another usage of this invention is colorimetric measurements where the intensity of light beam is first measured without any sample and then through the sample. From the measuring results the absorption value of the sample is calculated. In this respect this invention refers to the instruments usually called photometric platereaders. Still another usage of this invention is a chemiluminescence counter, where optical emissions due to chemical reactions are counted from an upper side of the well. In this respect this invention refers to the instruments usually called plateluminometers.

BRIEF DESCRIPTION OF THE DRAWINGS

Other advantages of the invention will become apparent from the following detailed description and by referring to the drawings where.

DETAILED DESCRIPTION OF THE PREFERRED EMBODIMENT

Figure 1:
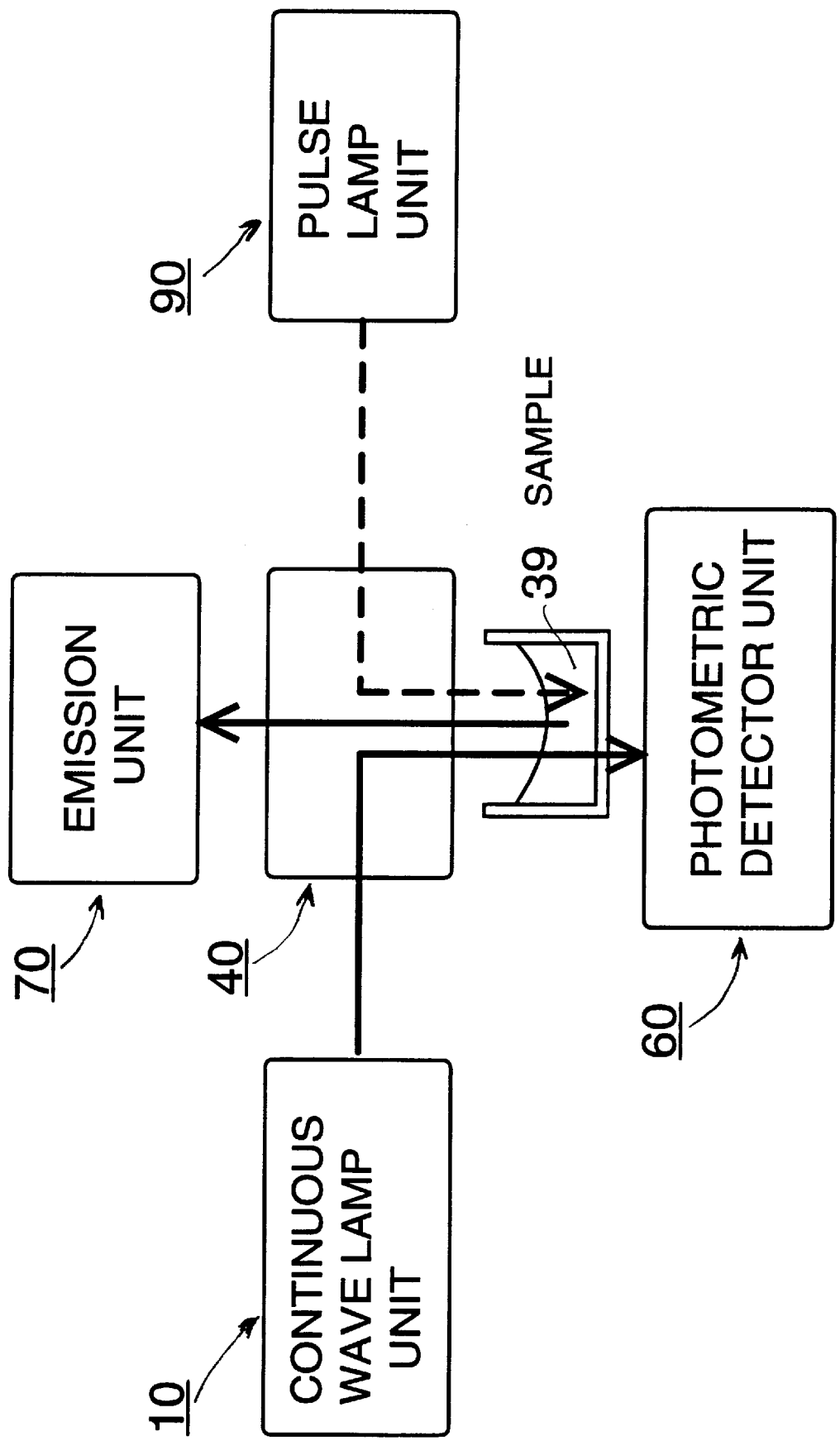
FIG. 1 is a schematic block diagram of the units of the preferred embodiment of the optical instrument including also an optional pulse-lamp unit.

FIG. 1 is presented a schematic block diagram of the units of the preferred embodiment of the present invention comprising a cw-lamp unit 10, an optomechanical coupling unit 40, a photometric detector unit 60, an emission unit 70, and a pulse-lamp unit 90.

Figure 2:
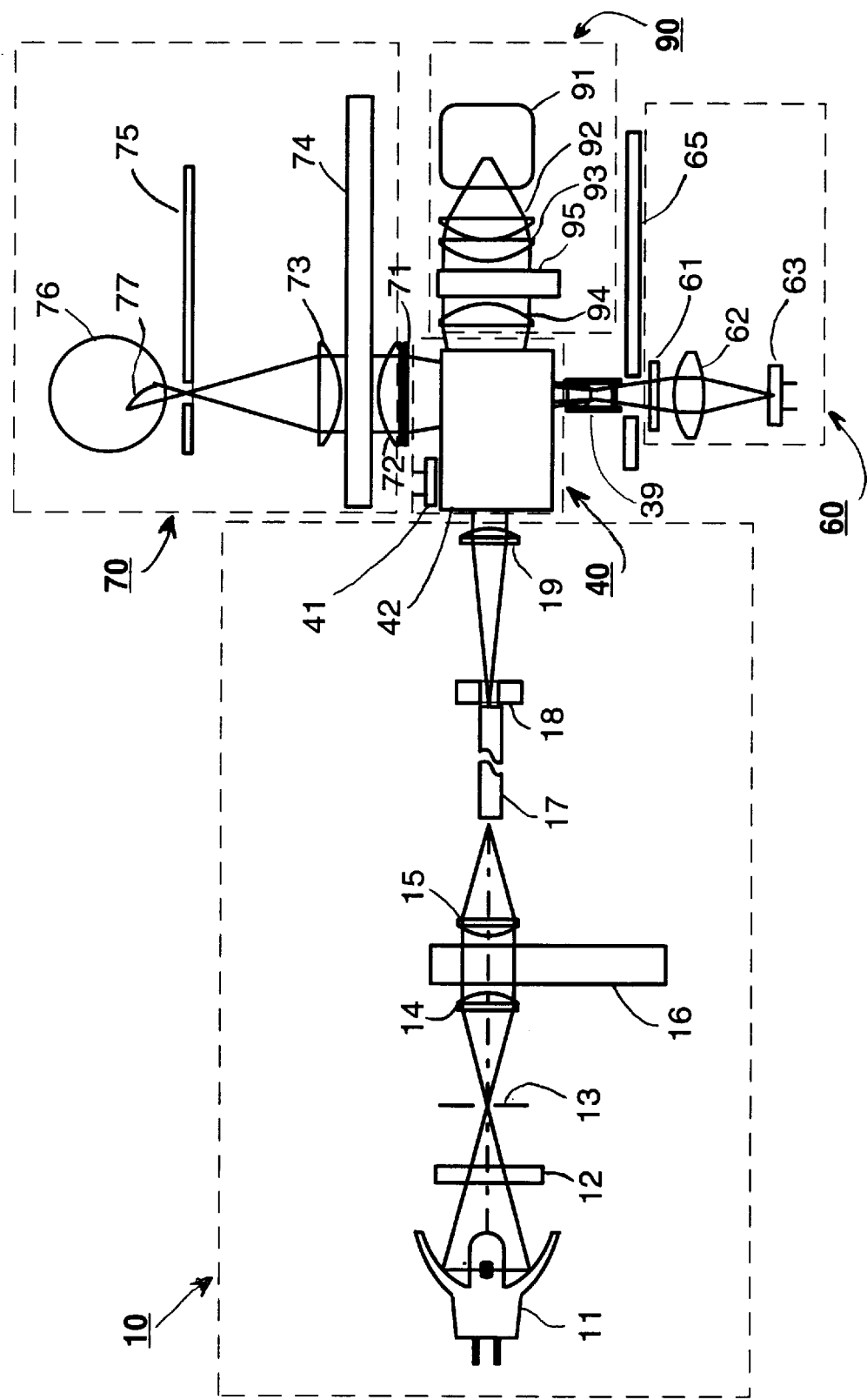
FIG. 2 is a detailed illustration of the components and the different optical paths of a preferred embodiment of the optical instrument including an optional pulse-lamp unit.

In FIG. 2 is the detailed illustration of the components and the different optical paths of a preferred embodiment of the optical instrument. The lamp 11 in the cw-lamp unit 10 is a tungsten-halogen filament reflector lamp (e.g. OSRAM, 12 V, 75 W, dichroic ultra-violet reflector) and it is used both for continuous wave fluorescence excitation and for absorption measurements. This lamp has enough power to generate optical radiation for photoluminescence excitation between 350 and 700 nm and for absorption measurements from 400 to 700 nm.

The infrared part of radiation from the said lamp 11 is absorbed by a tempered Schott KG2-glass filter 12 of thickness of 4 mm. After the stray-light aperture plate 13 of diameter of 6 mm the optical radiation is collimated with a lens 14 through an interference filter (not shown) located in a filter wheel 16 (details shown in FIG. 3). The lens 14 is an ultraviolet antireflection coated lens with a focal length of 25 mm and a diameter of 14 mm.

Then the light beam is focused with a lens 15, similar to the lens 14, into a liquid light guide 17 which has an effective diameter of 3 mm and a length of 500 mm. It isolates the measuring head thermally and mechanically. It also shields the measuring unit for the stray light from the cw-lamp.

The liquid light guide 17 has a very high ultraviolet transmission and a low infrared transmission. Using the liquid light guide instead of a glass fibre bundle ensures that no IR-radiation will reach the sample and heat it.

For the wavelength selection purposes there are different optical filters in a filterwheel 16. The same wheel 16 can be used in both fluorescence excitation and in absorption measurements. Although the fluorescence excitation filters are typically broader and better blocked than absorption filters, this arrangement allows using the installed filters in both technologies.

The simultaneous measurement of fluorescence and absorption at the same wavelength can be used to control the reliability of the fluorescence measurement. If exciting radiation is too highly absorbed the consequent emission is not linearly depending on the concentration of fluorescent molecules.

The stabilized optical radiation for fluorescence excitation is also user adjustable to help the user to find the optimum linear range of the chemistry and to fit it inside the linear range of the instrument.

The optical radiation from an output aperture plate 18, diameter of about 2 mm, of the light guide 17, is collimated with a lens 19, similar to the lens 14. The radiation beam is reflected inside a mirror block 42 and passed through a sample well 39 and hits an entrance window 61 of the photometric detector unit 60.

An important unit of present invention is the optomechanical coupling unit 40. It comprises a reference detector 41 and the mirror block 42 (Shown in details in FIG. 5). It is located on the upper side of the sample. Its function is to reflect the horizontal light beam from the selected lamp downwards to the sample and to reflect a portion of this beam into the reference photodiode and also to allow the emission from the sample to travel upwards to the photon counting detector 76.

The photometric detector unit 60 is located under the support plate 65 of plate holder, not shown. The photometric detector 63 is a large area silicon photodiode.

The entrance window 61, made of plastics, effectively absorbs ultra-violet radiation below 395 nm, i.e. the entrance window 61 also works as an ultraviolet cut-off filter. Its low intrinsic fluorescence emission is important in fluorescence measurements when using transparent sample wells. Ultraviolet radiation would cause photoluminescence in optical components of the photometric detector unit 60 and this would be detected as increased background fluorescence. This is most critical in time-resolved luminescence measurements because the average excitation energies are high.

The window 61 also protects underlying components from dust and liquid spill-outs. In the front of the detector 63 there is an aspheric biconvex lens 62 with focal length of 17.5 mm, and a diameter of 20 mm. The lens 62 compensates the diverging effects of the surface meniscus of the liquid sample 39. Thus the performance of the photometer is independent of the shape of the sample surface. Another function of the lens 62 is to destroy multiple reflections between the flat sample bottoms and the surface of the photodiode.

The emission unit 70 comprises optical components which are a filter 71 in filterslide 74 (Shown in FIG. 6), a combined shutter and aperture slide 75 (Shown in FIG. 7) and a detector 76, preferably a photomultiplier. In photon emission measurements a certain solid angle of an optical emission is collected from the upper side of the sample independently whether the emission is due to optical stimulation or chemical reaction.

Said solid angle is determined by the design of the emission optics. The emission optics comprises a ultraviolet cut-off filter 71 (diameter=25 mm, thickness=1 mm) and two plano-convex plastic lenses 72 and 73 (both of focal length= 40 mm and of diameter=25 mm), one lens for collecting the light from the sample and another lens for directing it into the aperture slide 75 in front of the detector 76.

The low fluorescent ultraviolet cut-off filter 71 in the front of the emission optics components prevents the ultraviolet radiation below 395 nm from reaching the other optical components inside the emission unit. The ultraviolet radiation generates undefined background emission in optical components or on other surfaces. Especially standard optical glasses used e.g. as cover glasses or thin-film substrates in interference filters are always fluorescent. Some color filter glasses often used as components in interference filters are highly fluorescent.

Figure 6:
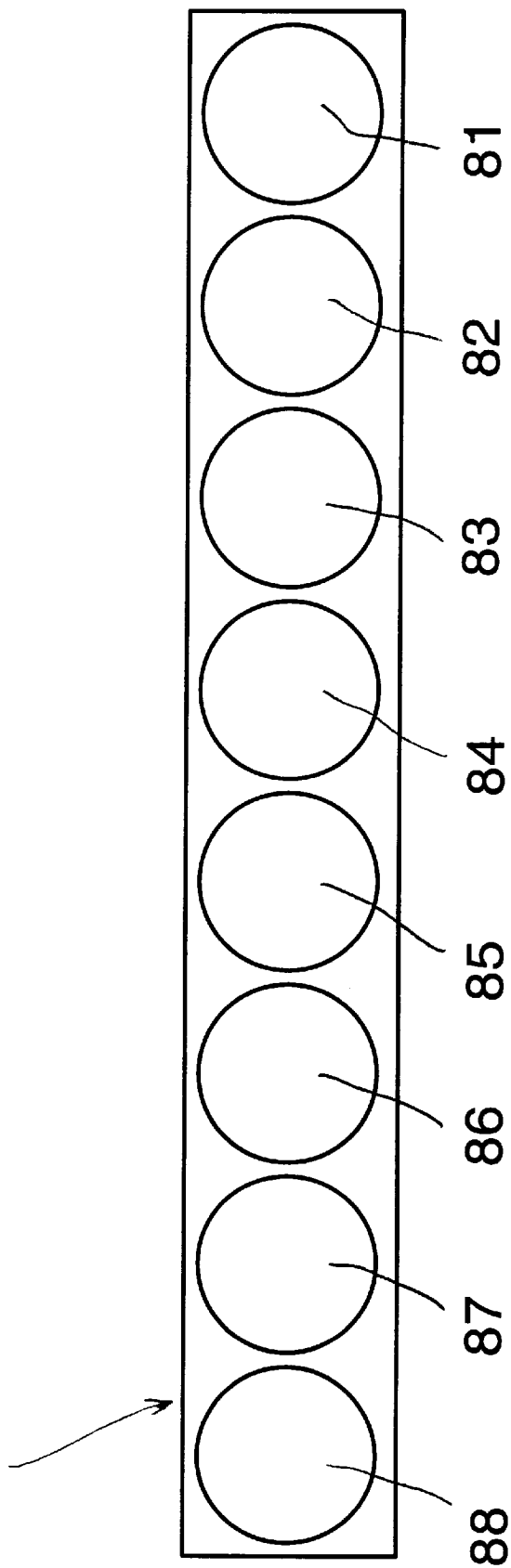
FIG. 6 is a schematic illustration of a filter slide in the emission unit.

Between the lenses 72 and 73 there is an emission filter slide 74 (Shown in FIG. 6). The filter slide position is in the collimated part of the beam to ensure the optimum performance of the interference filter utilized.

The aperture slide 75 is located at the average image point of the excited sample, which means that the area from which the optical emission is collected, can be selected with an aperture slide. In the present embodiment this suffers from the poor image quality of simple plano-convex lenses. For higher requirements the lenses 72 and 73 could be replaced by plastic aspheric lenses. For the highest performance the lenses 72 and 73 should be replaced by high-quality imaging lenses.

A photomultiplier tube 76 is used in all photon emission measurements as a detector. The used detector is a side window-type tube, as Hamamatsu R1527. This tube has a low-noise high-temperature cathode 77. The usable spectral range with this tube goes up to 700 nm which is enough for the photoluminescence emission from rare-earth chelates and for the most other labels.

New infrared fluorescence labels need a tube that is more infrared sensitive. The standard tube can easily be replaced by this kind of tube.

The photomultiplier 76 is used in the fast photon counting mode where the pulses from photomultiplier anode are first amplified and then fed through the fast comparator and the gate to the counter. The comparator rejects the pulses which are lower than the pre-adjusted reference level. This is a known advantage of single photon counting. The low pulses which more probably are noise pulses than true photon pulses, can easily be rejected in single photon counting technology. In analogue or current measuring technology contribution of these low pulses cannot be separated. True dark counts originating from the photo-cathode cannot be separated from real photon counts at all. The standard tube used in this instrument has only a few tens of true dark counts in one second.

The fast counting electronics is equipped with a gate in front of the counter. This gate is used in overall timings of the measurements but specially it is needed in time-resolved fluorescence measurements.

The pulse-lamp unit 90 is used in time-resolved photoluminescence measurement of rare-earth chelate labels or any other substance which shows phosphorescence or other long-living luminescence emission. It comprises a lamp 91, lenses 92–94 and optical filters in the filter slide 95 (Shown in FIG. 8) for wavelength isolation. Due to the relatively long decay-times of the rare-earth chelate labels the standard commercial flash-bulbs are suitable for excitation of these labels. The excitation pulse width of these low pressure discharge lamp is below one microsecond and no radiation tail exists after 50 μs of the pulse. The color temperature of these lamps is about 6000° K. That is why these lamps are suitable for ultraviolet excitation. But spectral distribution of these lamps depends on the temperature of the xenon gas inside the lamp bulb and the radiation spectrum of consequent pulses is different from each other so that this excitation system needs efficient stabilization of the excitation energy for every single measurement.

Still referring to FIG. 2 the whole measuring head comprising an emission unit 70, a coupling unit 40, the output end of the light guide 17 including the aperture 18, a lens 19 and an optional pulse-lamp unit 60 can be moved up and down depending on the sample type to be measured. Due to the aperture slide 75 the optimum emission region is of the size of the sphere with the same diameter as the diameter of aperture in the slide 75.

When measuring a fluorescent solution in a well the measuring height is not very critical but when measuring the dry bottom of the well or a filter fixed on the top of the well the measuring height should be adjusted respectively.

The sample plate movements are accomplished by conventional mechanical technology used in preceding instruments of the company. The plate holder (not shown is figures) moves the sample plate on the support plate 65. Individual measuring positions are defined in user protocols.

Figure 3:
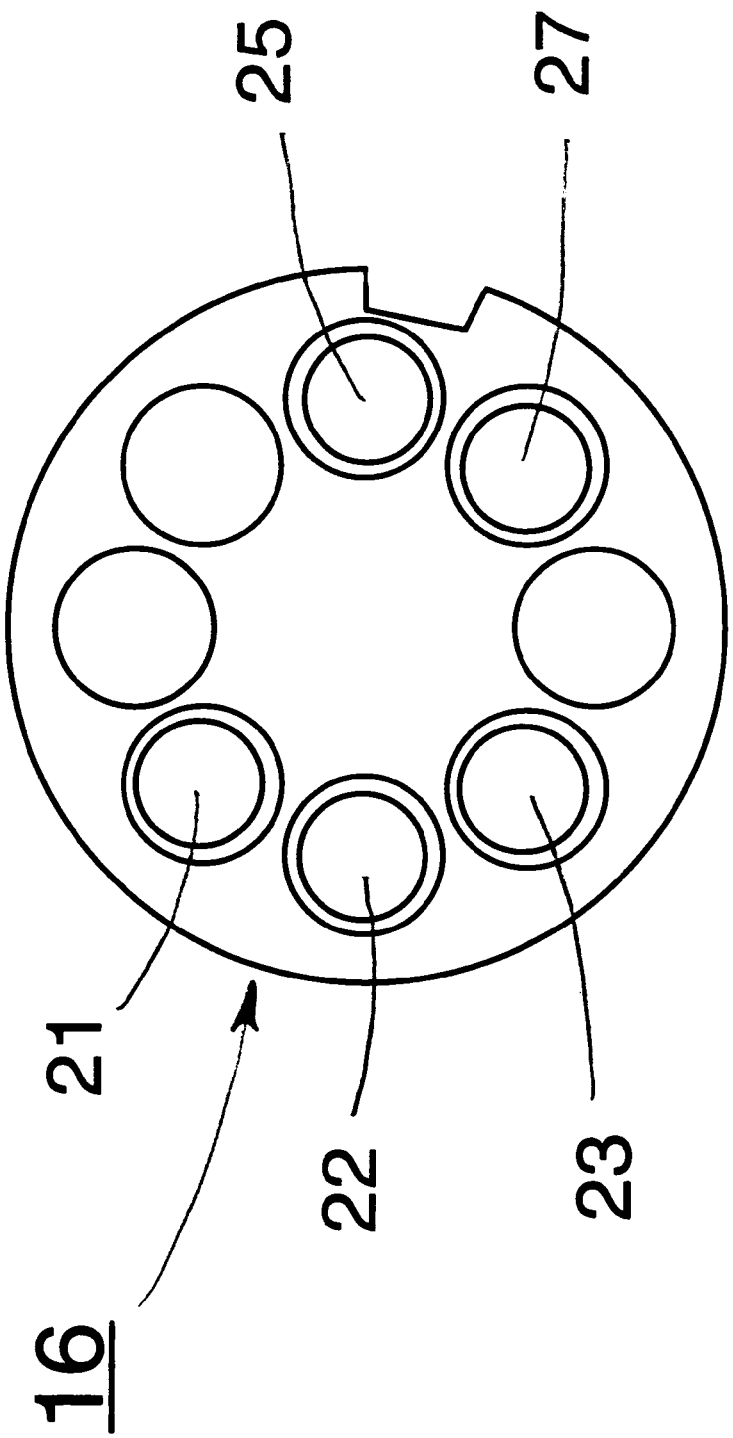
FIG. 3 is a schematic illustration of the standard 8-position filter wheel for fluorometry and photometry.
Figure 4:
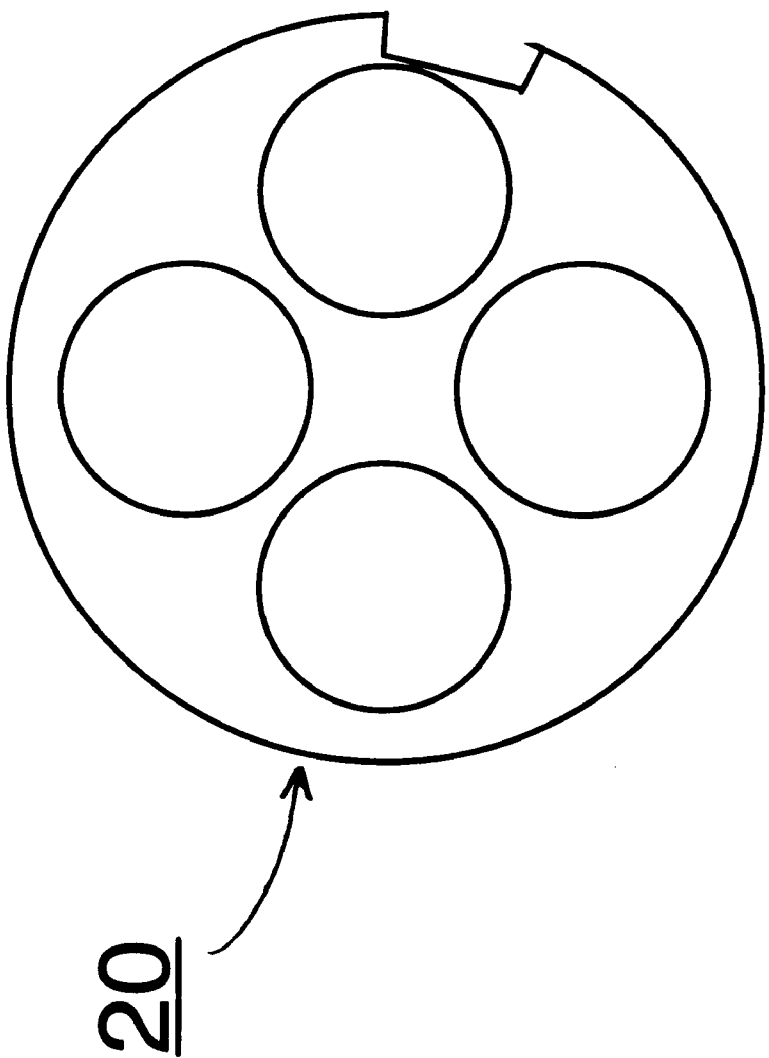
FIG. 4 is a schematic illustration of the alternative 4-position filter wheel for fluorometry and photometry.

A standard filter wheel 16 for the cw-lamp is shown in FIG. 3. It is an 8-position wheel equipped with five filters. Three of them are meant for common photometric wavelengths i.e. 405 nm filter 21, 450 nm filter 22 and 490 nm filter 23 and the other two are meant for common fluorescence excitation wavelengths, i.e. 355 nm filter 27 and 485 nm filter 25. All standard filters are high quality interference filters of diameter of 15 mm. Another configuration of the filter wheel 20 used in the preferred embodiment is shown in FIG. 4. It has only four filter positions for circular filters of diameter of 25.4 mm.

Figure 5:
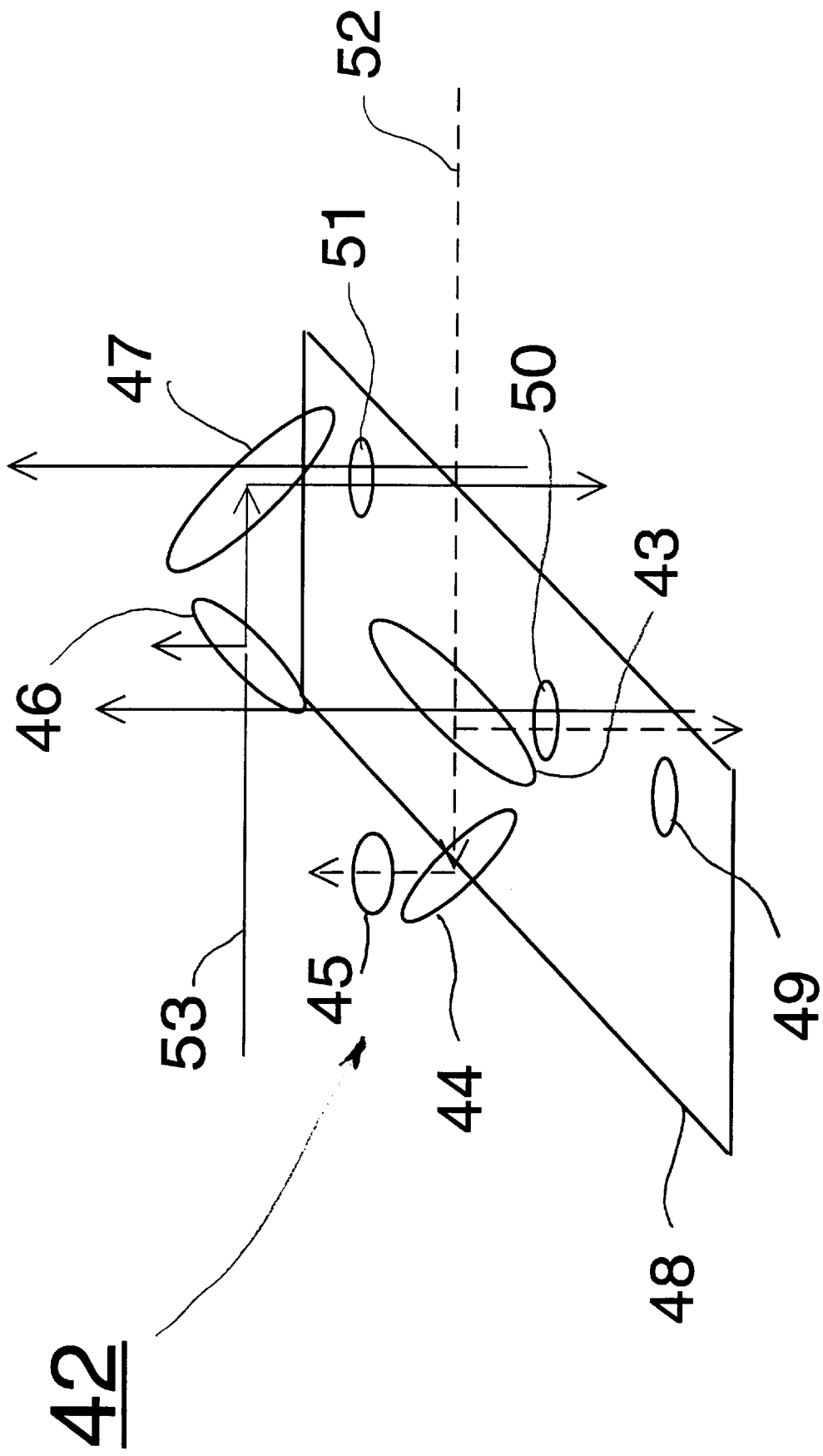
FIG. 5 is a schematic illustration of a mirror block of an optical coupling unit.

Now referring to FIG. 5, the mirror block 42 comprises four reflecting optical components, one filter and an aperture plate. The mirror block 42 is moved between three positions. The first position is used in fluorescence and absorption measurements. The radiation from the cw-lamp side first hits the reference beamsplitter 46, where about 30% of the intensity is reflected into the reference photodiode 41. The rest of the beam passes through the reference beamsplitter 46 and is reflected downwards from the main mirror 47, because it is aligned at the angle of 45 degrees at the beam coming from the cw-lamp via the liquid light guide. This mirror 47 is a small front surface aluminum mirror evaporated on a large quartz substrate. Due to this small mirror on the large substrate the emission light from a sample passes through an unevaporated part of this substrate to the detector 76 in FIG. 2. Only a smaller part of the emission light is lost in the mirror 47, but in conventional fluorescence measurements the collection efficiency is not very critical. This optical arrangement allows using the same mirror for different labels independent of their excitation and emission wavelengths or even totally different types of optical measurement, i.e. reflectance used in paper chromatography or stimulated phosphorescence from phosphor image plates.

Still referring to FIG. 5, a second position of the mirror block 42 is used only in time-resolved photoluminescence measurements and there the exciting radiation from flashlamp side first hits the main mirror 43 where most of the light is reflected downwards. This mirror is a thin-film dichroic mirror on a quartz substrate specified to have maximum reflectance in a near UV-region from 300 to 400 nm and maximum transmission in the visible region of the optical spectrum, specially from 500 to 700 nm, where all the emission bands of rare earth chelates are. The mirror 43 is aligned the at an angle of 45 degrees at the beam coming from a flashlamp. A small portion of the excitation light passes through the main mirror 43 and is reflected from the aluminum mirror 44 upwards through the filter 45 to the reference photodiode 41. The filter 45 absorbs the possible infrared band from the flashlamp excitation beam.

Due to the to block movements and the orthogonal alignment of reference mirrors only one reference detector component is needed. The detector used here is an ultraviolet enchanced silicon photodiode of size of 5.9×5.9 mm. A photodiode is connected to the operational amplifier and other electronics which function differently whether there is a pulse-lamp or a cw-lamp excitation to be stabilized. The location of the reference detector is optically about the same as the sample because it is important that the reference circuit sees all the same variations of the excitation beam as the sample.

Still referring to FIG. 5, the third position of the block is used for chemical luminescence and this part comprises no other optical component as an aperture 49 of 6 mm in the aperture plate 48. The aperture plate has also its own apertures for other positions of the block, the apertures 50, 51 to limit the exciting beam to hit the edges of the sample well or other adjacent samples and to stop the unwanted emission from the edges of the sample well or from the neighbouring well to reach the detector. The beams 52 and 53 refer to a time-resolved fluorescence exitation beam path and a fluorescence exitation beam path respectively.

The orthogonal alignment of the main mirrors 43, 47 of the block is the way to select the excitation source.

Now referring to FIG. 6, the filter slide 74 has 8 positions for filters of most common size of about one inch i.e. diameter of 25.4 mm. Four positions of the standard 8-position emission filter slide will be used for emission filters of rare-earth chelates labels, i.e. Europium (615) 81, Samarium (642) 82, Terbium (545) 83 and Dysprosium (572) 84. All these filters are high-quality interference filters with quite narrow (6–8 nm) bandwidths and exceptionally high peak transmissions (>70%). The filter position 87 at the standard slide is kept empty for chemical luminescence measurements but the user can specify any of the filters also to use with chemiluminescent samples. The two filter positions 85 and 86 are for the excitation filters of conventional fluorescence at wavelengths of 460 and 535 nm. As excitation and emission pairs the wavelengths 355/460 and 485/535 are used for as an example umbelliferone and fluorescein, respectively.

Figure 7:
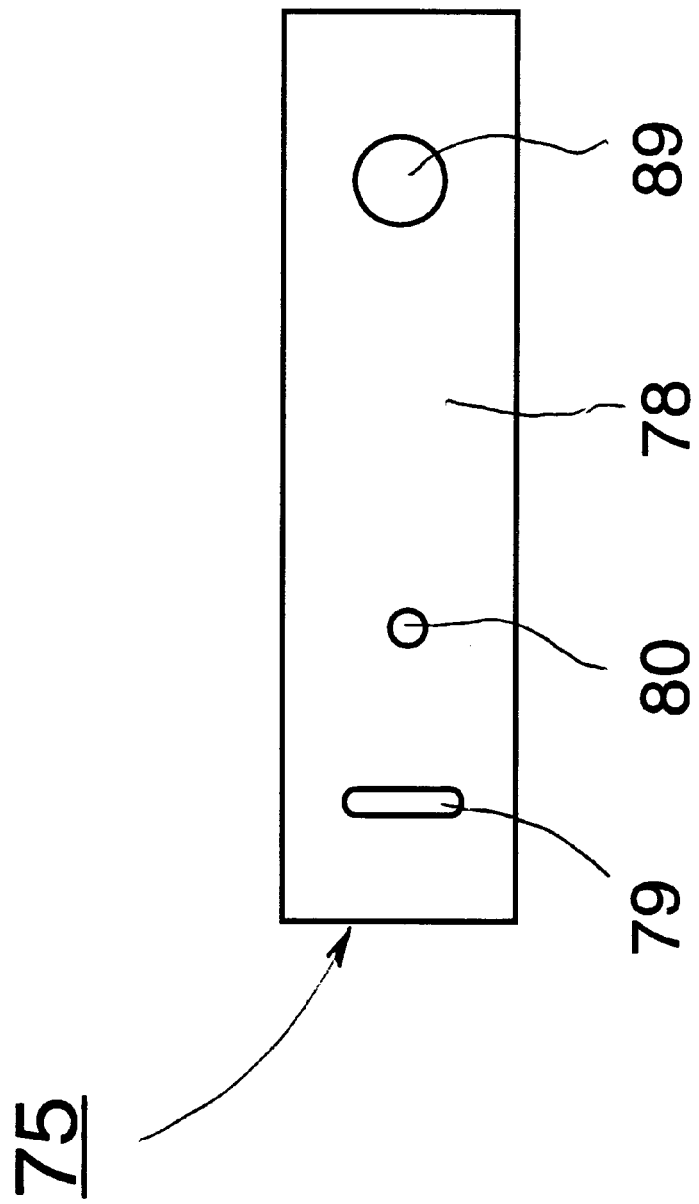
FIG. 7 is a schematic illustration of an aperture slide in an emission unit near the upper detector.

Now referring to FIG. 7, the aperture slide 75 of the emission unit has four positions, one is a shutter position 78, one aperture 79 has a longitudinal shape (about 3 mm×1 mm) and the two last apertures 89, 80 are circular with areas in ratio of 10:1. The different circular apertures are useful when controlling high emission of some fluorescent or luminescent assays. Also the cross-talk between adjacent wells depends on the size of the aperture.

Figure 8:
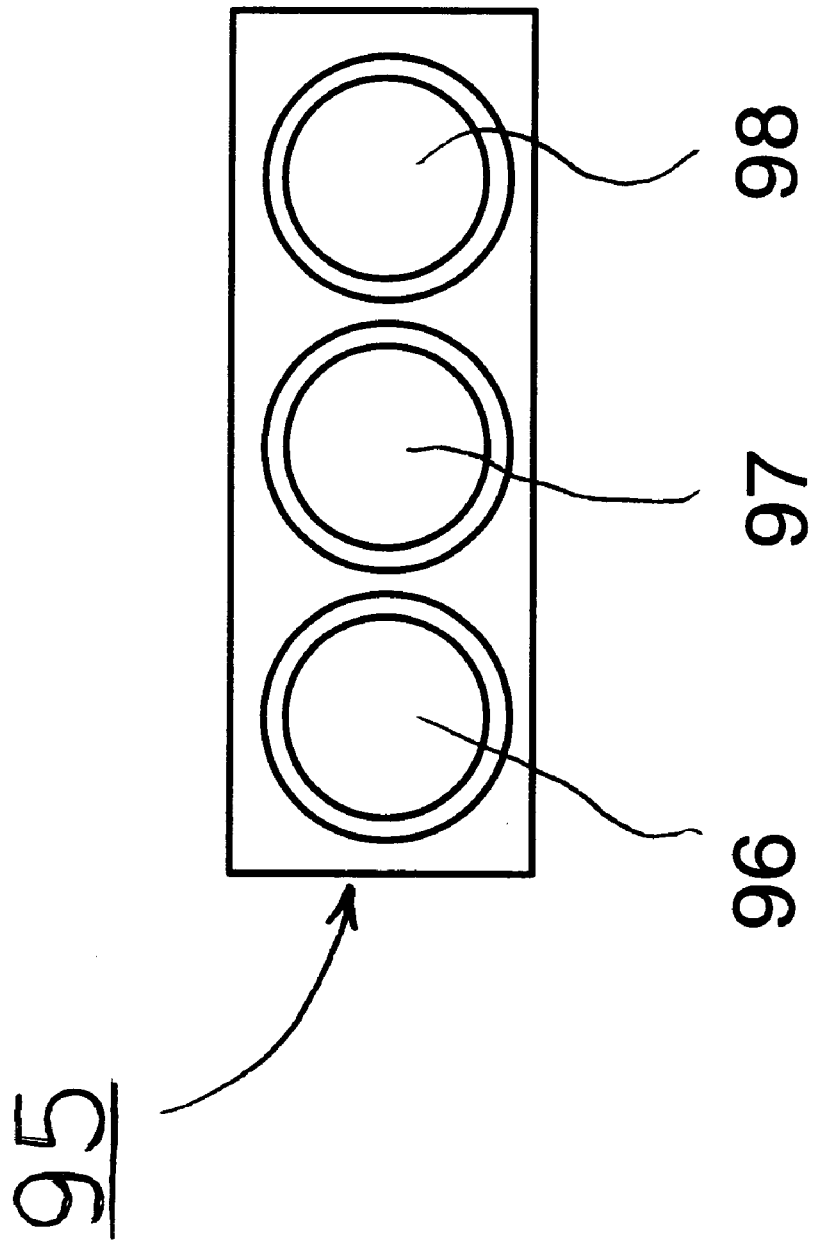
FIG. 8 is a schematic illustration of a filter slide in the pulse-lamp unit.

The excitation filter slide 95 of the pulse lamp unit is shown in detail in FIG. 8. There are three excitation filters 96–98 in the flash lamp excitation path. They are all broad band color glass filters or combinations of these filters transmitting in the ultraviolet region peaked at 340 nm filter 96, 320 nm filter 97, and 390 nm filter 98. The first filter 96 is used in all factory set labels, the second filter 97 includes the band of the first one but has lower edge at deeper ultraviolet radiation allowing excitation below 300 nm. The third filter 98 has an excitation band from 360 to 400 nm. These filters are not user changeable.

Now referring to another embodiment which does not include a pulse lamp unit. In this case the block is equipped only with the main mirror 47 and the reference mirror 46. Also the block itself can be shorter. In this embodiment the user is capable of measuring photoluminescence, absorption and chemical luminescence. The collection efficiency is in this case slightly smaller than without the main mirror 47.

Now referring back to FIG. 2. There are some advantages in the mutual arrangement of a dichroic mirror 43, a lens 94 and a lens 72. In the art an optical design of fluorescence instruments like a microscope is known there where is a common lens on top of the sample. This lens focuses exciting radiation and collecting emission radiation. The disadvantage of this design is that the fluorescence in this common lens causes background in the measurement.

Applications of the Invention

In the following is described a process where the optical instrument is used to perform measurements of different types of samples.

Fluorescence Measuring

Most fluorescence labels are based on a molecular fluorescence process. In this process optical radiation is absorbed by the ground state of a molecule. Due to the absorption of energy quantum the molecule rises into a higher excited state. After the fast vibrational relaxation the molecule returns back to its ground state and the excess energy is released as an optical quantum. Due to losses in this process the average absorbed energies are always higher than the average emitted energies.

The time scale in these molecular processes is in the region of nanoseconds. Therefore the fast time scale time-resolved detection of molecular fluorescence is rather complicated. That is why the conventional fluorescence measurements are performed without any time-discrimination using continuous wave excitation source and continuous detection. In this invention the kind of measurements are performed using the stable continuous excitation source and the single photon counting detection method.

Figure 9:
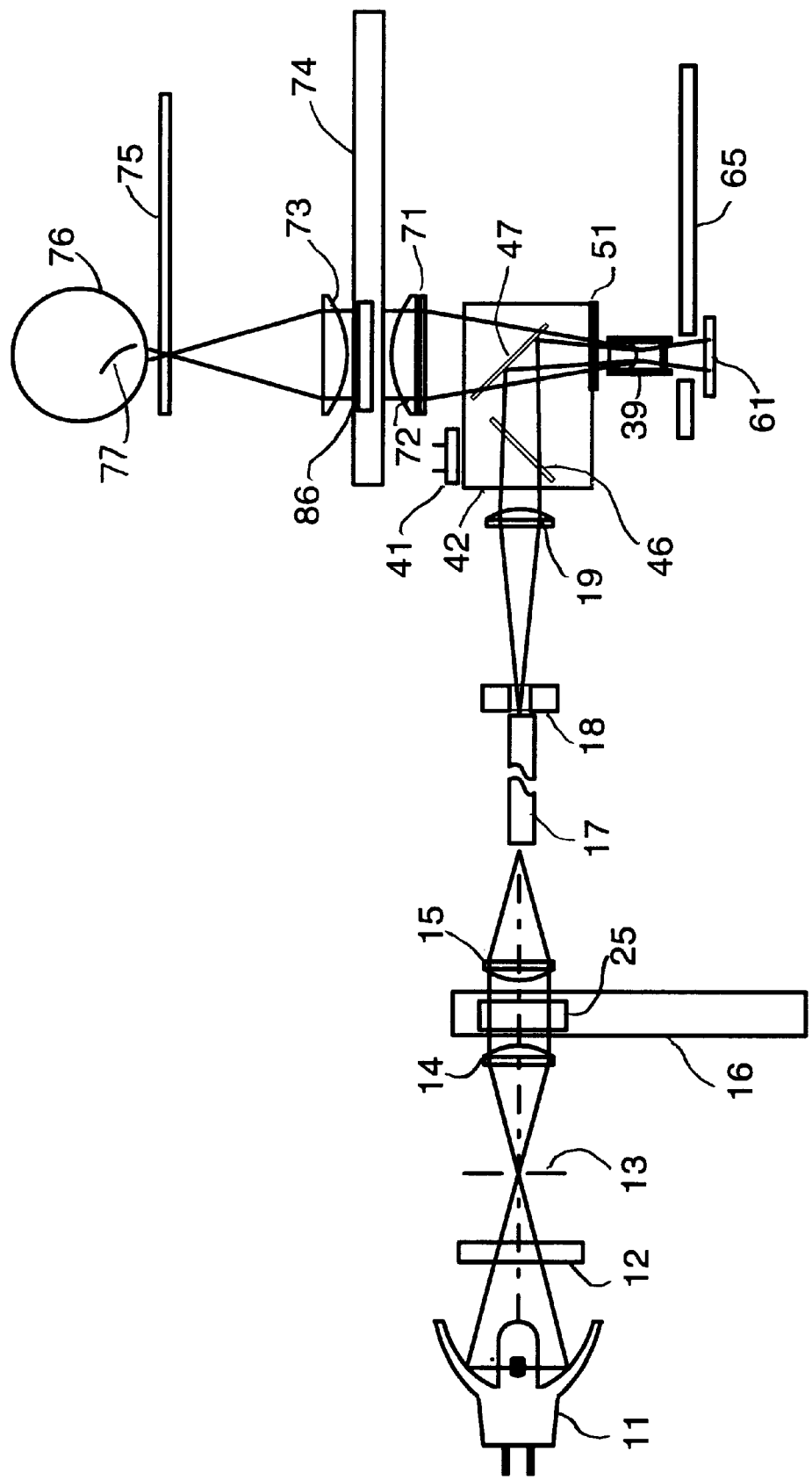
FIG. 9 is a schematic illustration of the optical paths and the components used in photoluminescence measurements.

One common fluorescent label is fluorescein and its derivatives, of which excitation and emission wavelengths are about 490 and 515 nm, respectively. Now referring to the FIG. 9, to measure the fluorescent emission from the sample containing fluorescein, an excitation light beam from the cw-lamp 11 is applied through an appropriate filter 25 into the light guide from where it is collimated with the lens 19 and directed through the sample well 39 into the entrance window 61 of the photometric detector. The consequent emission is deviated into all directions and a moderate portion of it is collimated with a lens 72 through the appropriate interference filter 86 and then directed with the lens 73 through the aperture of aperture slide 75 and into the detector 76. The pulses from the photomultiplier are amplified and discriminated in a comparator and fed through the gate into the counter. The gate, controlled by programmable instrument settings, is opened for a counting time, typically one second. Before opening the gate the excitation power is switched on and stabilized to the predetermined level. After the measurements the lamp is switched off to spare the lamp and to keep the instrument cooler.

However cw-excitation and cw-detection can always be used to measure all kinds of photoluminescence phenomena, like delayed fluorescent, phosphorescence, and time-resolved photoluminescence.

There is some special fluorescence methods where a special label are excited alternately with two different wavelengths. These measurements refer often to research work done with calcium-ions. The sample is excited alternately with two different excitation wavelengths and the ratio of corresponding emission intensities is determined. The value of the ratio depends of the calcium-ion concentration. Using the filter 20 shown in FIG. 4 these measurements can be performed with the instrument described in this invention. The filter wheel is equipped with two pairs of both types of excitation filter so that the two adjacent filters are always different. Just by rotating the filter wheel at appropriate speed and by counting emission synchronously the ratio can be measured.

Absorption Measurements

In the photometric measurement the intensity of a filtered and stabilized beam is first measured without any sample and then the sample inside one plate is measured. The absorbance i.e. the absorption values are then calculated from the equation $A = -\log(I/I_0)$, where $I_0$=the light intensity measured without any sample I=the intensity after the absorbing and reflecting medium.

Because the optical surfaces of the empty well reflect backward about 8% of optical energy the measured absorption values are always about 0.04 A (absorbance) for an empty clear plate.

Figure 10:
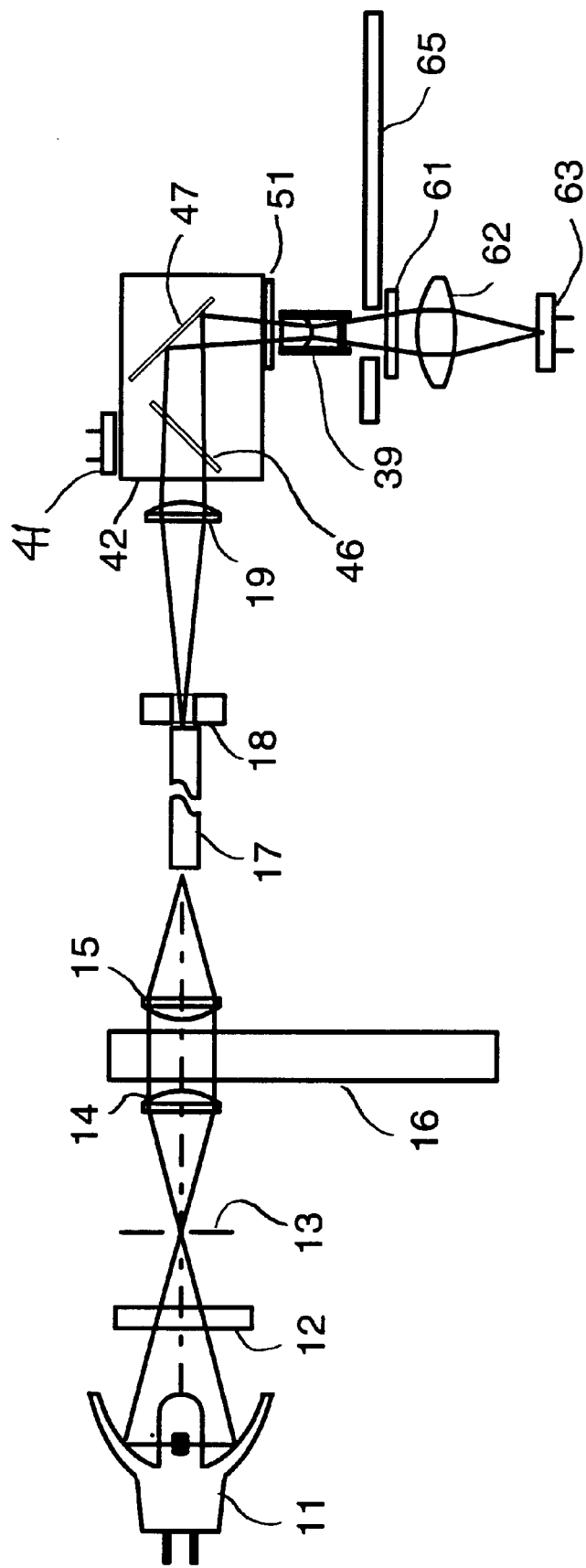
FIG. 10 is a schematic illustration of the optical paths and the components used in absorption measurements.

FIG. 10 shows the components of the optical instrument when performing absorption measurements.

In the case of such an embodiment, where only conventional fluorescence measurements with the cw-lamp excitation is done, the entrance window 61 and the lens 62 could be made of pure silica or other ultra-violet transmitting material, thus allowing the measurement of also absorption values in the ultraviolet region. This means that an absorption of the fluorescent sample could also be measured at the lowest fluorescence excitation region, about 355 nm, and these values could be used to check that the sample fluorescence is in the linear region or even to make some corrections.

Chemiluminescence Measuring

Figure 11:
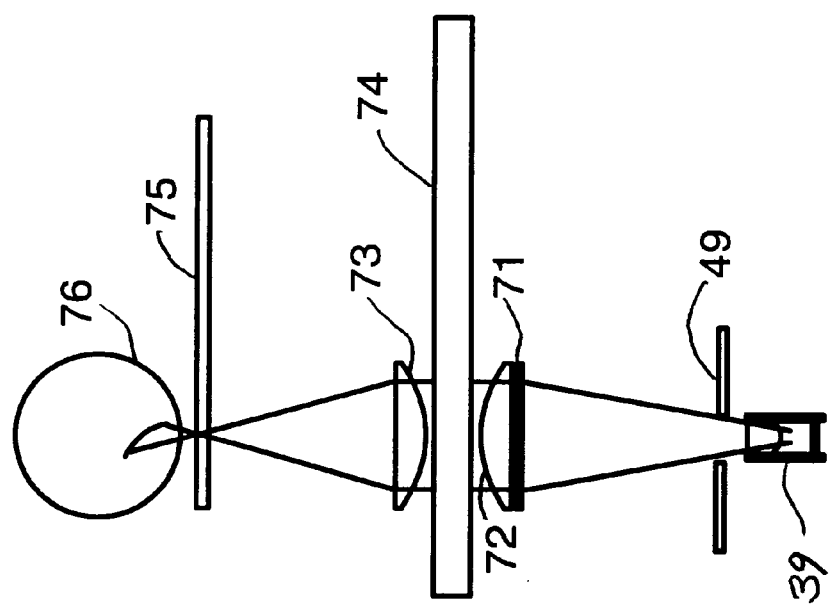
FIG. 11 is a schematic illustration of the optical paths and the components used in chemical luminescence measurements.
Figure 12:
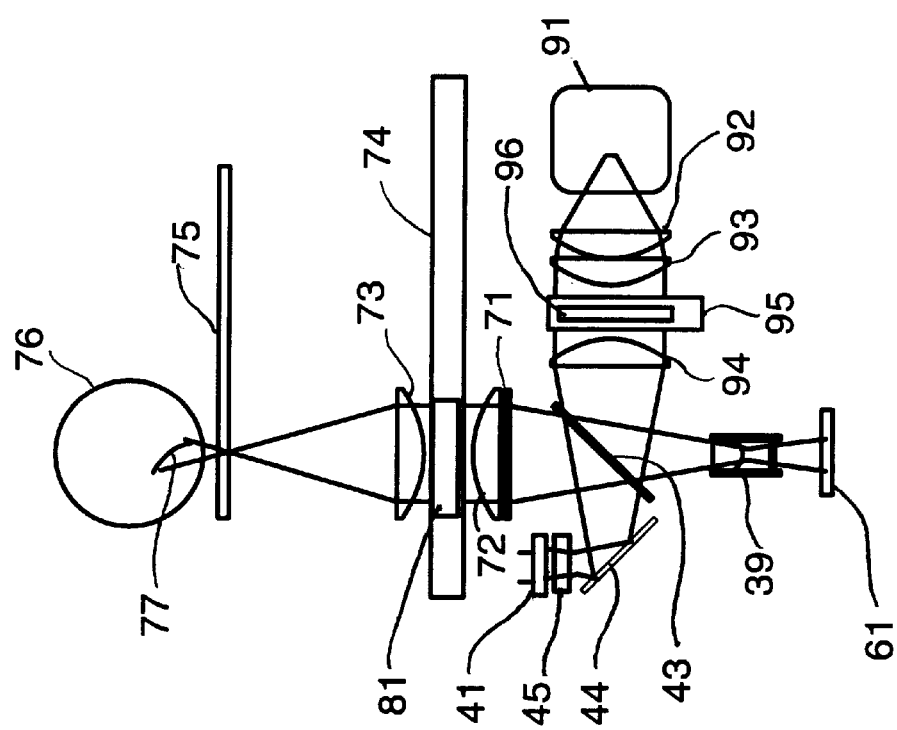
FIG. 12 is a schematic illustration of the optical paths and the components used in time-resolved photoluminescence measurements.

Typically the instruments designed for measuring a glow type chemiluminescence from the microtitration plate are quite simple. Optical radiation emitting from the sample is collected most effectively and detected with a system capable of wide linear range. Any fluorometer can also be used as a luminometer. Noting, however, that very seldom the optimum design for a fluorometer is an optimum design for a luminometer. This is also the case with the present invention. The components of the preferred embodiment of this invention used in chemical fluorescence measurements are shown in FIG. 11. Typically luminometers do not have any filters, but there are now chemical luminescent assays having two measurements emissions and to measure this assay the filter slide 74 is useful. Also many modern luminescent assays produce much light and therefore the smaller aperture 80 shown in FIG. 7 can be very important.

Time-resolved Photoluminescence Measuring

Because the decay times of the rare-earth chelates are fairly long, i.e. from ten microseconds to a few thousand microseconds, the measuring system for these labels is not very complicated compared to nanosecond fluorometry. The decay time of the rare earth chelate depends on its actual configuration. But for example the chelates used in the DELFIA (R) system by Wallac have decay times of about 730 $\mu$s. The measuring cycle in time-resolved measurement comprises a excitation pulse, a delay time, which is dependent on the decay time of the label and the nature and time behavior of background radiation, a counting window time and then dwell time before a next excitation pulse. With the Europium-label the optimum values for timings are, 400, 400 and 200 us. The sum of these values is the cycle time. One millisecond cycle time means a flash pulse frequency of 1 KHz which is also a typical maximum pulse rate for lamps.

Now referring to a Europium-chelate in solution, the sample 39 is excited by short, below 1 μs and intense ultra-violet pulse, e.g. ca 500 nJ, from the short-arc flashlamp 91. The optical radiation from the arc is collected and collimated with the lenses 92 and 93, filtered with the color glass filter 96 and directed with the lens 94 and the dichroic mirror 43 through the sample. The dichroic mirror 43 transmits a small portion of the excitation beam, which portion is reflected from the mirror 44 upwards through the filter 45 into the reference photodiode 41.

A portion of the generated photoluminescence is collected with a lens 72 filtered in a filter 81 and detected by a photomultiplier 76. A pulse train from the photomultiplier is amplified and filtered in a comparator and fed through an electronic gate to a counter. The counts in counting window for one measurement are accumulated until the predetermined value of the excitation energy is reached.

One measurement consist a number of excitation pulses, typically one thousand. The reference diode 41 integrates a portion of excitation energy and the value of integrated energy is used to stabilize the excitation energy between the separate measurements.

In the preferred embodiment the user can adjust various parameters of a measurement. The excitation pulse energy is adjusted by the discharge voltage and by the capacitors of the flashlamp power supply. Total excitation energy of one measurement is adjusted by choosing different integrator capacitors for a reference circuit and by changing a reference level of the integrator. Also all timing parameters of the time-resolved measurements are user adjustable.

Typical measuring time in standard labels is about one second for one well and about 2–3 minutes for a 96-well plate. But in all measurement types the user can change the measurement time for one well/for example/to 0.1 second and consequently the measurement time for the whole plate can be about 50 seconds. The decreasing measurement time decreases the number of the count and thus due to the poisson statistics increases the coefficient of the variation. In the fluorescence measurements the excitation energy can be increased knowing that the linear range of the counter is dependent on the measurement time.

With a counting time of one second the linear range of the counter alone is almost 6 decades but with 0.1 second measurement time it is a decade less. Specially in the time resolved measurement the variations of the excitation energies between subsequent measurements depend on the numbers of flashes in one measurement. If the number of flashes is about 1000 as in all factory set labels, the variation is below 0.1%. But if the number of flashes in one measurement is only about 100, as it could be with suitable parameters, the variations in excitation energies are close to 1%, which means that the coefficient of the variation can be doubled inside one plate. Still these instrumental errors are often small compared to other sample handling errors.

Other Methods

An experienced user is able the use the present invention also in other measurement technologies in common use in biochemical laboratories. Now referring to FIG. 9, e.g. reflectance, turbidimetric and nephelometric measurement can be measured using a fluorescent measurement technology with the exception that the emission filter in the slide 74 must be a gray filter.

Now referring to FIG. 2, although the invention is described with the arrangement where the light lamps and photomultiplier detector are on the upper side of the sample and the photometric detector is below the sample, there is no reason why this invention should not work also vice versa.

Although the invention has been described with reference to the different microtitration plates it is equally applicable to any form of sample matrix like gels and filters.

I claim:

1. A multilabel measurement instrument for performing photoluminescence and chemical luminescence measurements of a sample (39) on a sample support, the instrument comprising;

a cw-lamp (11), a mirror block (42) having a mirror (47) and at least one aperture(49), and a detector (76), the mirror block being provided with first and second sections so that the mirror block (42) is movable between first and second positions, whereby when the mirror block is moved to the first position, the first section of the mirror block (42) provides a first optical path (53) from the cw-lamp (11) via the mirror (47) to the sample (39) and a second optical path from the sample through the mirror (47) to the detector (76) in order to perform a photoluminescence measurement, and when the mirror block (42) is moved to the second position, the second section of the mirror block (42) provides a third optical path from the sample (39) to the detector (76) via the aperture (49) in order to perform a chemical luminescence measurement.

2. A multilabel measurement instrument for performing photoluminescence, chemical luminescence and absorbance measurements of a sample (39) on a sample support, the instrument comprising a cw lamp (11), a mirror block (42) having a mirror (47) and at least one aperture (49), and first and second detectors (76, 63), the mirror block being provided with first and second sections so that the mirror block (42) is movable between first and second positions, whereby when the mirror block (42) is moved to the first position, the first section of the mirror block (42) provides a first optical path (53) from the cw-lamp (11) via the mirror (47) to the sample (39) and a second optical path from the sample through the mirror (47) to the first detector (76) in order to perform a photoluminescence measurement, and in the first position, the first section of the mirror block (42) further provides a fourth optical path (53) from the cw-lamp (11) via the mirror (47) through the sample (39) to the second detector (63) in order to perform an absorbance measurement, and when the mirror block (42) is moved to the second position, the second section of the mirror block (42) provides a third optical path from the sample (39) to the first detector (76) via the aperture (49), in order to perform a chemical luminescence measurement.

3. A multilabel measurement instrument for performing photoluminescence, chemical luminescence, absorbance and time-resolved photoluminescence measurements of a sample (39) on a sample support, the instrument comprising a cw-lamp (11), a pulse lamp (91), a mirror block (42) having first and second mirrors (47, 43) and at least one aperture (49), and first and second detectors (76, 63), the mirror block being provided with first, second and third sections so that the mirror block (42) is movable between first, second and third positions, whereby when the mirror block (42) is moved to the first position, the first section of the mirror block (42) provides a first optical path (53) from the cw-lamp (11) via the first mirror (47) to the sample (39) and a second optical path from the sample (39) through the first mirror (47) to first detector (76) in order to perform a photoluminescence measurement, and in the said first position, the first section of the mirror block (42) further provides a fourth optical path from the cw-lamp (11) via the first mirror (47) through the sample (39) to the second detector (63) in order to perform an absorbance measurement, when the mirror block (42) is moved to the second position, the second section of the mirror block (42) provides a third optical path from the sample (39) to the first detector (76) via the aperture (49) in order to perform a chemical luminescence measurement, and when the mirror block (42) is moved to the third position, the third section of the mirror block (42) provides a fifth optical path from the pulse lamp (91) via the second mirror (43) to the sample and a sixth optical path from the sample through the second mirror to the first detector in order to perform a time-resolved photoluminescence measurement.

4. A multilabel measurement instrument for performing photoluminescence, chemical luminescence, absorbance and time-resolved photoluminescence measurements of a sample (39) on a sample support, the instrument comprising a cw-lamp (11), a pulse lamp (91), a mirror block (42) having first and second mirrors (47, 43), first and second reference mirrors (46, 44) and at least one aperture (49), first and second detectors (76, 63), and a reference detector (41), the mirror block (42) being provided with first, second and third sections so that the mirror block (42) is movable between first, second and third positions, whereby when the mirror block (42) is moved to the first position, the first section of the mirror block (42) provides a first optical path (53) from the cw-lamp (11) via the first mirror (47) to the sample (39), a second optical path from the sample through the first mirror (47) to the first detector (76) in order to perform a photoluminescence measurement and a seventh optical path from the cw-lamp (11) via the first reference mirror (46) to reference detector (41) in order to stabilize the cw-lamp, and in the said first position, the first section of the mirror block (42) further provides a fourth optical path (53) from the cw-lamp (11) via the first mirror (47) through the sample (39) to the second detector (63) in order to perform an absorbance measurement, when the mirror block (42) is moved to the second position, the second section of the mirror block (42) provides a third optical path from the sample (39) to the first detector (76) via the said aperture (49) in order to perform a chemical luminescence measurement, and when the mirror block (42)is moved to the third position, the third section of the mirror block (42) provides a fifth optical path from the pulse lamp (91) via the second mirror (43) to the sample (39) and a sixth optical path from the sample (39) through the second mirror (43) to the first detector in order to perform a chemical time-resolved photoluminescence measurement and an eighth optical path from the pulse lamp (91) via the second reference mirror (44) to reference detector (41) in order to stabilize the pulse lamp (91).

* * * * *